United States Patent
Jensen et al.

(10) Patent No.: US 6,569,880 B2
(45) Date of Patent: *May 27, 2003

(54) BIS(BENZIMIDAZOLE) DERIVATIVES SERVING AS POTASSIUM BLOCKING AGENTS

(75) Inventors: Bo Skaaning Jensen, Copenhagen S (DK); Søren Peter Olesen, Klampenborg (DK); Lene Teuber, Værløse (DK); Dan Peters, Arlöv (SE); Dorte Strøbæk, Farum (DK)

(73) Assignee: Neurosearch A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/084,179

(22) Filed: Feb. 28, 2002

(65) Prior Publication Data

US 2002/0137784 A1 Sep. 26, 2002

Related U.S. Application Data

(62) Division of application No. 09/750,345, filed on Dec. 29, 2000, now Pat. No. 6,380,180, which is a division of application No. 09/347,514, filed on Jul. 2, 1999, now Pat. No. 6,194,447.
(60) Provisional application No. 60/092,218, filed on Jul. 8, 1998.

(30) Foreign Application Priority Data

Jul. 2, 1998 (DK) .................................. DK 1998 00865

(51) Int. Cl.[7] .................. A61K 31/4184; C07D 403/08
(52) U.S. Cl. ..................... 514/388; 514/394; 548/305.4
(58) Field of Search ....................... 548/305.4; 514/388, 514/394

(56) References Cited

U.S. PATENT DOCUMENTS

| | | | |
|---|---|---|---|
| 4,004,016 A | 1/1977 | Yale et al. |
| 5,190,976 A | 3/1993 | Weber et al. |
| 5,739,127 A | 4/1998 | Schohe-Loop et al. |
| 5,760,230 A | 6/1998 | Schohe-Loop et al. |
| 5,866,562 A | 2/1999 | Schohe-Loop et al. |
| 5,874,438 A | 2/1999 | Schohe-Loop et al. |
| 6,174,897 B1 | 1/2001 | Schohe-Loop et al. |

FOREIGN PATENT DOCUMENTS

| | | |
|---|---|---|
| EP | 0 520200 | 12/1992 |
| EP | 0 545845 | 6/1993 |
| EP | 0 604353 | 6/1994 |
| FR | 1 532237 | 7/1968 |
| WO | WO9118868 | 12/1991 |
| WO | WO9422807 | 10/1994 |
| WO | WO9748705 | 12/1997 |

OTHER PUBLICATIONS

Siro et al., Tetrahedron, vol. 54, No. 9 (1998) pp. 1929–1936.
Gholamkhass et al., J. Phys. Chem. B., vol. 101, No. 44 (1997) pp. 9010–9021.
Paolini et al., CA, vol. 62 (1965) pp. 16229b.
Antons et al., CA, vol. 124 (1996) pp. 261039.
Prasad et al., CA, vol. 124 (1996) pp. 276799.
Kuecuekbay et al., CA, vol. 124 (1996) pp. 232388.
Downing et al., CA, vol. 123 (1995) pp. 55882.
Doelling et al., CA, vol. 123 (1995) pp. 83322.
Galanakis et al., CA, vol. 123 (1995) pp. 83169.
Jois et al., CA, vol. 123 (1994) pp. 299422.
Bobosik et al., CA, vol. 120 (1994) pp. 30719.
Bulgarevich et al., CA, vol. 118 (1993) pp. 101303.
Selezneva et al., CA, vol. 117 (1992) pp. 171307.
Ohno et al., CA, vol. 116 (1992) pp. 94388.
Adebayo et al., CA, vol. 112 (1990) pp. 77039.
Anders et al., CA, vol. 111 (1989) pp. 173956.
Pujar et al., CA, vol. 110 (1989) pp. 204616.
Elguero et al., CA, vol. 107 (1987) pp. 197386.
Safronova et al., CA, vol. 103 (1985) pp. 6405.
Julia et al., CA, vol. 102 (1985) pp. 45842.
Kashima et al., CA, vol. 101 (1984) pp. 151793.
Meth–Cohn et al., CA, vol. 97 (1982) pp. 6213.
Ogata et al., CA, vol. 94 (1981) pp. 30647.
Boguslaski et al., CA, vol. 94 (1981) pp. 1788.
Popov et al., CA, vol. 89 (1978) pp. 109239.
Sawlewicz et al., CA, vol. 89 (1978) pp. 6277.
Krasovskii et al., CA, vol. 85 (1976) pp. 123891.
Tkachenko et al., CA, vol. 82 (1975) pp. 57611.

(List continued on next page.)

Primary Examiner—Laura L. Stockton
(74) Attorney, Agent, or Firm—Birch, Stewart, Kolasch & Birch, LLP

(57) ABSTRACT

This invention relates to novel potassium channel blocking agents, and their use in the preparation of pharmaceutical compositions.

Moreover the invention is directed to pharmaceutical compositions useful for the treatment or alleviation of diseases or disorders associated with the activity of potassium channels, in particular asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

5 Claims, No Drawings

OTHER PUBLICATIONS

Medvedeva et al., CA, vol. 78 (1973) pp. 43360.
Maynard et al., CA, vol. 75 (1971) pp. 110235.
Maulding et al., CA, vol. 68 (1968) pp. 38860.
Acheson et al., CA, vol. 67 (1967) pp. 11455.
Reimlinger et al., CA, vol. 76 (1972) pp. 140718.
Aries, CA, vol. 71 (1969) pp. 38960.
Kuz'menko et al., CA, vol. 118 (1993) pp. 6913.
Nanvyan et al., CA, vol. 106 (1987) pp. 176254.
Makarov et al., CA, vol. 99 (1983) pp. 5708.
Database Crossfire, XP002119054, BRN 5829311, 1992.
Chemical Abstracts, vol. 69, No. 25 (Dec. 16, 1968), XP002119051, p. 9665.
Database Crossfire, XP002119055, BRN 623197, 1962.
Gary E. Struve et al., Journal of Organic Chemistry, vol. 42, No. 25 (Dec. 9, 1977), XP002119045, pp. 4035–4040.
Adrian W. McConnaughie et al., Journal of Medicinal Chemistry, vol. 37, No. 8 (Apr. 15, 1994), XP002119046, pp. 1063–1069.
Database Crossfire, XP002119056, BRN 6073654, 1984.
Chemical Abstracts, vol. 126, No. 19 (May 12, 1997), XP002119052, p. 1162.
Zhiqiang Shi et al., Tetrahedron Letters, vol. 36, No. 16 (1995), XP002119047, pp. 2741–2744.
Zhiqiang Shi et al., Journal of Organic Chemistry, vol. 60, No. 18 (sep. 8, 1995), XP002119048, pp. 5935–5945.
Joaquin Campos Rosa et al., Journal of Medicinal Chemistry, vol. 41, No. 1 (Jan. 1, 1998), XP002119049, pp. 2–5.
Hans Reimlinger et al., Chemische Berichte, vol. 105, No. 3, (Mar. 3, 1972), XP002119044, pp. 794–798.
Chemical Abstracts, XP002119050, vol. 78, No. 7 (Feb. 19, 1973), XP002119050, p. 481.
Database Crossfire, XP002119053, BRN 4580162 and 4559969, 1982.
Pujar et al., CA 101:182621 (1984).
Shi et al., Tetrahedron Letters, vol. 36, No. 16, pp. 2741–2744 (Apr. 17, 1995).
Rajakumar et al., Tetrahedron Letters, vol. 38, No. 30, pp. 5323–5326 (Jul. 28, 1997).
Shi et al., J. Org. Chem., vol. 60, No. 18, pp. 5935–5945 (Sep. 8, 1995).

BIS(BENZIMIDAZOLE) DERIVATIVES SERVING AS POTASSIUM BLOCKING AGENTS

This application is a divisional of application Ser. No. 09/750,345 filed on Dec. 29, 2000 now U.S. Pat. No. 6,380,180, which is a divisional of application Ser. No. 09/347,514 filed on Jul. 2, 1999, now U.S. Pat. No. 6,194,447, which is a conversion of Provisional Application No.: 60/092,218 filed Jul. 8, 1998, the entire contents of which are hereby incorporated by reference and for which priority is claimed under 35 U.S.C. §120; and this application claims priority of Application No. PA 1998 00865 filed in Denmark on Jul. 2, 1998 under 35 U.S.C. §119.

TECHNICAL FIELD

This invention relates to novel potassium channel blocking agents, and their use in the preparation of pharmaceutical compositions.

Moreover the invention is directed to pharmaceutical compositions useful for the treatment or alleviation of diseases or disorders associated with the activity of potassium channels, in particular asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

BACKGROUND ART

Ion channels are transmembrane proteins, which catalyze the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

A number of neuromuscular blocking agents with effect on SK channels exist, e.g. apamin, atracurium, pancuronium and tubocurarine.

WO 97/48705 discloses a particular group of chemical compounds useful as calcium activated potassium channel blocking agents. However, their selectivity in respect of the SK channel is not disclosed.

U.S. Pat. Nos. 5,739,127 and 5,760,230 disclose other groups of chemical compounds acting on potassium channels.

SUMMARY OF THE INVENTION

The present invention resides in the provision of novel chemical compounds capable of selectively blocking SK channels, or subtypes of SK channels.

Moreover the invention is directed to pharmaceutical compositions useful or the treatment or alleviation of diseases or disorders associated with the activity of potassium channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

Accordingly, in its first aspect, the invention provides novel chemical compound of the invention is one selected from the group represented by the general formulas I to VIII, below.

In another aspect, the invention provides pharmaceutical compositions comprising an effective amount of a chemical compound of the invention.

In further aspects the invention relates to the use of a chemical compound of the invention for the manufacture of a medicament for the treatment or alleviation of diseases or disorders associated with the activity of potassium channels, and to method of treatment or alleviation of disorders or conditions responsive to blockade of potassium channels.

DETAILED DISCLOSURE OF THE INVENTION

Potassium Channel Blocking Agents

In its first aspect, the invention provides novel chemical compounds. The chemical compounds of the invention is particularly useful as potassium channel blocking agents.

Thus, the invention provides a potassium channel blocking agent, in particular a SK channel blocking agent, selected from the group represented by the general formulas I to VIII, below.

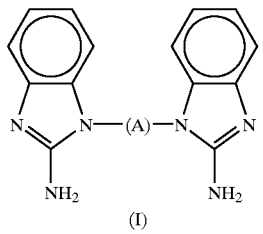

Formula I a bis(aminobenzimidazole) derivative, wherein

A represents a spacing group containing of from 1 to 20 atoms, a spacing group having a chain length of from 1 to 20 atoms, or a spacing group having a chain length comprising of from 1 to 20 separate bonds.

The spacing group, A, may in particular be a linear or branched alkylene chain having of from 1 to 15 carbon atoms, which alkylene group may be interrupted by one or more oxygen or sulphur atoms, or by one or more groups of the formula —NR'—, or =NR', wherein R' represents hydrogen or alkyl;

a radical of the formula —(CH$_2$)$_a$-D-(CH$_2$)$_b$—, wherein a and b, which may be identical or different, represent the number 0, 1, 2, 3, 4 or 5, and D represents a cycloalkyl group; or an aryl group of from 6 to 12 carbon atoms, which aryl group may in particular be a phenyl group or a biphenyl group.

In a most preferred embodiment, A is a spacing group selected from those A-groups described in the working examples and in Tables 1, 7 and 8, below, and those B-groups described in the working examples and in Table 8, below.

In a most preferred embodiment, the compound of Formula I is 1,3-Bis[(2-aminobenzimidazol-1-yl)methyl]cyclohexane;
1,6-Bis(2-aminobenzimidazol-1-yl)hexane;
1,4-Bis(2-aminobenzimidazol-1-yl)butane;
1,3-Bis(2-aminobenzimidazol-1-yl)propane;
1,2-Bis(2-aminobenzimidazol-1-yl)ethane;
α,α'-Bis(2-aminobenzimidazol-1-yl)-para-xylene;
α,α'-Bis(2-aminobenzimidazol-1-yl)-meta-xylene;
1,3-Bis(2-aminobenzimidazol-1-yl)benzene;
3,3'-Bis(2-aminobenzimidazol-1-yl)biphenyl; or
cis-1,5-bis(2-amino-1-benzimidazolyl)cyclooctane.

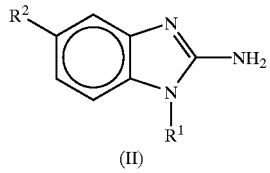

Formula II an aminobenzimidazole derivative, wherein

R$^1$ represents a mono- or polycyclic aryl group, an aralkyl group, or a mono- or poly-heterocyclic group, which aryl, aralkyl and heterocyclic groups may optionally be substituted one or more times with substituents selected among halogen; alkyl; alkoxy; cyano; trifluoromethyl; phenyl; guanidino, which guanidino may optionally be substituted with alkyl, phenyl or benzyl; primary, secondary or tertiary amino groups, i.e. an amino group substituted once or twice with an alkyl group (—NH$_2$; —NH-alkyl; and —N(alkyl)$_2$); or a mono- or polycyclic aryl group as described above, attached to a mono- or poly-heterocyclic group described above; and R$^2$ represents hydrogen, an alkyl group, or CF$_3$.

An example of a preferred aryl group is phenyl.
An example of a preferred aralkyl group is benzyl.
Examples of preferred heterocyclic groups are pyrazolyl, imidazolyl, thiazolyl, and isothiazolyl.

In a more preferred embodiment R$^1$ is a mono- or polycyclic aryl group or a mono- or poly-heterocyclic group selected from those R$^1$-groups described in the working examples and in Table 2, below. In a more preferred embodiment R$^1$ is phenyl, benzyl, pyrazolyl, imidazolyl, thiazolyl, or isothiazolyl.

In a most preferred embodiment R$^2$ represents a substituent selected from those R$^2$-groups described in the working examples and in Table 2, below.

In a most preferred embodiment, the compound of Formula II is

2-Amino-1-[4-(4-chlorophenyl)-2-thiazolyl]benzimidazole;
2-Amino-1-(4-dimethylaminobenzyl)-5-trifluoromethylbenzimidazole;
2-Amino-1-(4-phenyl-2-thiazolyl)benzimidazole;
2-Amino-1-[3-(1,3,5-trimethylpyrazol-4-yl)phenyl]benzimidazole;
2-Amino-1-(4-(N-(2-thiazolyl)amino)phenyl)benzimidazole;
1-(4-(2-Aminobenzimidazol-1-yl)phenyl)-3-phenylguanidine;
2-Amino-1-(4-acetamidophenyl)benzimidazole; or
2-Amino-1-(4-aminophenyl)-benzimidazole.

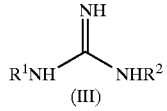

Formula III a guanidine derivative, wherein

R$^1$ and R$^2$, which may be identical or different, represent hydrogen, alkyl, a mono- or poly-heterocyclic group, a mono- or polycyclic aryl group, or an aralkyl group, which heterocyclic, aryl or aralkyl groups may optionally be substituted one or more times with substituents selected among halogen; alkyl; alkoxy; cyano; trifluoromethyl; phenyl; guanidino, which guanidino may optionally be substituted with alkyl, phenyl or benzyl; or primary, secondary or tertiary amino groups, i.e. an amino group substituted once or twice with an alkyl group (—NH$_2$; —NH-alkyl; and —N(alkyl)$_2$).

Examples of preferred heterocyclic monocyclic groups of the invention are furanyl, imidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolyl, pyridazinyl, pyridyl, pyrimidinyl, pyrrolyl, thiadiazolyl, thiazolyl, and thienyl.

Examples of preferred heterocyclic polycyclic groups of the invention are benzimidazolyl, indolyl, isoquinolyl, quinolyl, acridinyl, phenazinyl, and phenthiazinyl.

Examples of preferred aryl groups of the invention are phenyl, naphthyl and anthracenyl.

A preferred aralkyl group of the invention is benzyl.

In a most preferred embodiment, $R^1$ represents substituent selected from those $R^1$-groups described in the working examples and in Table 3, below.

In a most preferred embodiment, $R^2$ represents a substituent selected from those $R^2$-groups described in the working examples and in Table 3, below.

In a most preferred embodiment the compound of Formula III is 1-(2-Methoxy-5-(trifluoromethyl)phenyl)-3-(3-(trifluoromethyl)phenyl)guanidine;
1-(4-Chlorobenzyl)-3-(3-triflouromethylphenyl)guanidine;
1-(5-Chloro-2-methoxyphenyl)-3-(3-(trifluoromethyl)phenyl)guanidine;
1,3-Bis(3-(trifluoromethyl)phenyl)guanidine;
1-(2-Bromo-5-(trifluoromethyl)phenyl)-3-(5-(trifluoromethyl)phenyl)guanidine;
1-(4-aminophenyl)guanidine;
α,α'-Bis(3-phenylguanidine-1-yl)-para-xylene; or
6-Amino-3-guanidinoacridine.

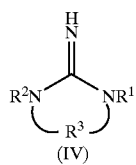

(IV)

Formula IV a guanidine derivative, wherein $R^1$ and $R^2$, which may be identical or different, represents hydrogen, a mono- or polycyclic aryl group, or an aralkyl group, which aryl or aralkyl groups may optionally be substituted one or more times with substituents selected among halogen, alkyl, alkoxy, cyano, trifluoromethyl, primary, secondary or tertiary amino groups, i.e. an amino group substituted once or twice with an alkyl group (—NH$_2$; —NH-alkyl; and —N(alkyl)$_2$); and $R^3$ represents a divalent mono- or poly-heterocyclic group, a divalent mono- or polycyclic aryl group, or a divalent aralkyl group, which heterocyclic, aryl, aralkyl may optionally be substituted one or more times with substituents selected among halogen, alkyl, alkoxy, cyano, trifluoromethyl, primary, secondary or tertiary amino groups, which secondary and tertiary amino groups may substituted (once or twice) with an alkyl group or a phenyl group, said phenyl group optionally being substituted one or more times with substituents selected among halogen, trifluoromethyl, and/or cyano;

a divalent radical of the formula —(CH$_2$)$_c$—, wherein c is a number 1, 2, 3, 4 or 5; or a mono- or polycyclic aryl group as described above, attached to another mono- or polycyclic aryl group as described above, optionally attached via an oxygen, sulphur, or nitrogen atom to form a divalent bridging group, in which bridging group the nitrogen atom may additionally be substituted with a mono- or polycyclic aryl group as described above to form a tertiary amino group.

Examples of preferred $R^1$ and $R^2$ groups are phenyl and benzyl, optionally substituted one or more times with halogen and/or a primary amino group. The substitutions may preferably be in the ortho- and/or para-positions.

Examples of preferred $R^3$ groups are divalent phenyl groups, or divalent phenyl groups bridged by a nitrogen atom to form a secondary or tertiary amino group, which tertiary amino group may preferably be substituted with an additional phenyl group, which phenyl group may optionally be substituted with halogen, trifluoromethyl or cyano.

In a most preferred embodiment $R^1$ represents a substituent selected from those $R^1$-groups described in the working examples and in Table 4, below.

In a most preferred embodiment $R^2$ represents a substituent selected from those $R^2$-groups described in the working examples and in Table 4, below.

In a most preferred embodiment $R^3$ represents a substituent selected from those $R^3$-groups described in the working examples and in Table 4, below.

In a most preferred embodiment the compound of Formula IV is

5-Chloro-1,3-bis-(4-chlorobenzyl)-2-iminobenzimidazoline;
12-(3-Chloro-4-cyanophenyl)-6-imino-5,7,12-triaza-dibenzo[a,f]cyclooctane;
1-(2-Aminophenyl)-2-imino-3-phenyl-imidazolidine; or
6-Imino-5,7,12-triaza-di-benzo[a,f]cyclooctane.

Formula V

R—L—R     (V)

representing symmetric compounds wherein

L represents a spacing group containing of from 1 to 20 atoms, a spacing group having of from 2 to 20 atoms, or a spacing group comprising of from 2 to 20 separate bonds; and R represents a mono- or polycyclic aryl group, an aralkyl group, or one or more mono- or poly-heterocyclic group(s), which heterocyclic group preferably comprises one or more nitrogen atoms as the heteroatom(s), or a mono- or polycyclic aryl group or an aryl group attached to a heterocyclic group as described above.

The R-group holding a tertiary nitrogen atom may in particular be made quaternary using an alkylation agent, preferably an alkyl halide, such as the chloride, bromide or iodide of methyl or ethyl.

The spacing group, L, may in particular be a linear or a branched alkylene chain having of from 2 to 5 carbon atoms;

a radical of the formula —(CH$_2$)$_a$-D-(CH$_2$)$_b$—, wherein a and b, which may be identical or different, represent the number 0, 1, 2, 3, 4 or 5, and D represents a cycloalkyl group;

an aryl group of from 6 to 12 carbon atoms, which aryl group may in particular be a biphenyl group; or a mono- or poly-heterocyclic group, which heterocyclic group preferably comprise one or more nitrogen atoms as the heteroatom(s).

An example of a preferred aryl group is phenyl.

Examples of preferred heterocyclic groups are pyrolidinyl, pyrrolyl, pyrazolyl, imidazolyl, pyridinyl, piperidinyl, pyridazinyl, pyrimidinyl, pyrazinyl, and piperazinyl.

The R group may preferably be a nitrogen containing heterocyclic ring attached to a nitrogen containing hetero-aromatic ring (heteroaryl), wherein the nitrogen containing heterocyclic ring preferably is piperazinyl, and the nitrogen containing heteroaryl preferably is pyrimidinyl; or a nitrogen containing hetero-aromatic ring (heteroaryl), wherein the nitrogen containing heterocyclic ring preferably is benzimidazolyl, attached to an aralkyl group, wherein the aralkyl group preferably is benzyl.

In a most preferred embodiment L represents a spacing group selected from those L-groups described in the working examples and in Table 5, below.

In a most preferred embodiment R represents a substituent selected from those R-groups described in the working examples and in Table 5, below.

In a most preferred embodiment the compound of Formula V is

α, α'-Bis(1-(2-pyrimidyl)piperazin-4-yl)-para-xylene;

α, α'-Bis(1-(2-pyrimidyl)-4-methylpiperazinium-4-yl)-para-xylene; or 1,4-Bis(1-benzylbenzimidazol-2-yl)piperazine.

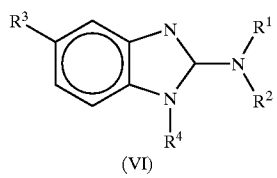

Formula VI (VI)

wherein $R^1$, $R^2$, and $R^4$, which may be identical or different, represent hydrogen, alkyl, phenyl or benzyl, which phenyl or benzyl may optionally be substituted one or more times with substituents selected among halogen, trifluoromethyl, and cyano; and $R^3$ represents hydrogen, halogen, trifluoromethyl, cyano, alkyl, phenyl or benzyl.

In a most preferred embodiment $R^1$ represents a substituent selected from those $R^1$-groups described in the working examples and in Table 6, below.

In a most preferred embodiment $R^2$ represents a substituent selected from those $R^2$-groups described in the working examples and in Table 6, below.

In a most preferred embodiment $R^3$ represents a substituent selected from those $R^3$-groups described in the working examples and in Table 6, below.

In a most preferred embodiment $R^4$ represents a substituent selected from those $R^4$-groups described in the working examples and in Table 6, below.

In a most preferred embodiment the compound of Formula VI is
1-(4'-Chlorobenzyl)-2-dimethylamino)-5-trifluoromethylbenzimidazoline.

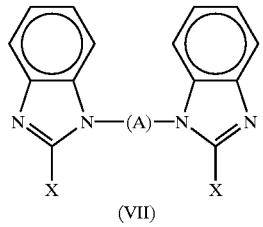

Formula VII (VII)

a bis(benzimidazole) derivative, wherein

A is a spacing group with the meanings described for group A under Formula I, above, and X represents hydrogen, halogen, trifluoromethyl, cyano, alkoxy, alkyl, phenyl or benzyl, which phenyl or benzyl may optionally be substituted one or more times with substituents selected among halogen, trifluoromethyl, and alkyl; or a mono- or poly-heterocyclic group, preferably comprising one or more nitrogen, oxygen or sulphur atoms as heteroatom(s), which heterocyclic group may optionally be substituted one or more times with substituents selected among halogen, trifluoromethyl, alkoxy or alkyl.

In a most preferred embodiment A represents a spacing group selected from those A-groups described in the working examples and in Table 7, below.

In a most preferred embodiment X represents a substituent selected from those X-groups described in the working examples and in Table 7, below.

In a most preferred embodiment the compound of Formula VII is cis,trans-1,4-Bis[(2-chlorobenzimidazol-1-yl)methyl]cyclohexane;

cis,trans-1,4-Bis[2-(1-pyrrolidinyl)benzimidazol-1-yl)methyl]cyclohexane;

cis,trans-1,4-Bis[(2-(4-morfolinyl)benzimidazol-1-yl)methyl]cyclohexane;

cis,trans-1,4-Bis[(2-(1-methylpiperazine-4-yl)benzimidazol-1-yl)methyl]cyclohexane; or α,α'-Bis(1-benzimidazolyl)-meta-xylene.

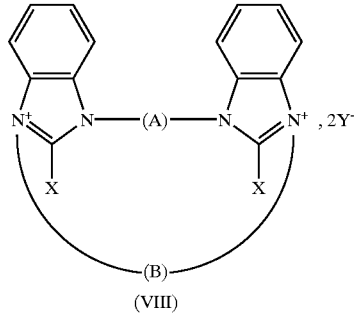

Formula VII (VIII)

a bis(benzimidazolium) derivative, wherein

A and B, which may be identical or different, represent spacing groups as described for group A under Formula I, above;

X is as described under Formula VII, above; and

Y represents a halide, and is preferably chlorine, bromine or iodine.

In a most preferred embodiment A and B represents a spacing group selected from those A-groups described in the working examples and in Tables 1, 7 and 8, below.

In a most preferred embodiment the compound of Formula VIII is 1,1'-(α,α'-para-xylylene)-3,3'-(α,α'-meta-xylylene)-bis(benzimidazolium).

Definition of Substituents

In the context of this invention a spacing group designates a substituent that links the two parts of the molecule and bring these parts into a relatively determined spatial inter-relationship. The spacing group may also be termed a linking group or a bridging group. The spacing group of the invention should link the two parts of the molecule in a not too close and not too far distance from each another. It is currently believed that spacing groups comprising of from 2 to 20 atoms fulfill this requirement. Examples of such spacing groups are described herein, and summarized below.

| Spacing Group | Name |
|---|---|
| —(CH$_2$)$_{10}$— | decamethylene; |
| —(CH$_2$)$_8$— | octamethylene; |
| —(CH$_2$)$_6$— | hexamethylene; |
| —(CH$_2$)$_5$— | pentamethylene; |
| —(CH$_2$)$_4$— | tetramethylene; |
| —(CH$_2$)$_3$— | trimethylene; |
| —(CH$_2$)$_2$— | dimethylene; |
| —N(CH$_3$)—CH$_2$—N(CH$_3$)— | N,N'-dimethyl-diamino-methylene; |
| —N(CH$_3$)—CH$_2$—CH$_2$—N(CH$_3$)— | N,N'-dimethyl-diamino-dimethylene; |
| —N(CH$_3$)—CH$_2$—CH$_2$—CH$_2$—N(CH$_3$)— | N,N'-dimethyl-diamino-trimethylene; |
| [structure] | (cis and/or trans)-1,5-cyclooctylene; |
| [structure] | (cis and/or trans)-1,3-dimethyl-cyclohexane-α,α'-diyl; |
| [structure] | para-xylene-α,α'-diyl; |
| [structure] | meta-xylene-α,α'-diyl; |
| [structure] | 1,3-phenylene; |
| [structure] | biphenyl-3,3'-diyl; |
| [structure] | 4,4'-dimethyl-bibenzyl-α,α'-diyl; |
| [structure] | 4,4'-dimethyl-diphenylmethane-α,α'-diyl; |

-continued

| Spacing Group | Name |
|---|---|
| [structure] | 4,4'-dimethyl-cis/trans-stilbene-α,α'-diyl; |
| [structure] | 2,6-bis(4'-methyl-phenyl)pyridine-α,α'-diyl; |
| [structure] | 3,3'-dimethyl-biphenyl-α,α'-diyl; |
| [structure] | 2,7-dimethyl-9H-fluorene-α,α'-diyl; |

In the context of this invention halogen represents a fluorine, a chlorine, a bromine or a iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention an alkoxy group designates an "alkyl-O-" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono- or polycyclic aryl group designates a monocyclic or polycyclic aromatic hydrocarbon group. Examples of preferred aryl groups of the invention are phenyl, naphthyl and anthracenyl.

In the context of this invention an aralkyl group designates a mono- or polycyclic aryl group as defined above, which aryl group is attached to an alkyl group as also defined above. An example of a preferred aralkyl group of the invention benzyl.

In the context of this invention a mono- or poly-heterocyclic group is a mono- or polycyclic compound, which holds one or more heteroatoms in its ring structure. One or more of the ring structures may in particular be aromatic (i.e. a heteroaryl). Preferred heterocyclic monocyclic groups of the invention are 5- or 6 membered heterocyclic monocyclic groups. Examples of preferred heterocyclic monocyclic groups of the invention are furanyl, imidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolyl, pyridazinyl, pyridyl, pyrimidinyl, pyrrolyl, thiadiazolyl, thiazolyl, and thienyl. Examples of preferred heterocyclic polycyclic groups of the invention are benzimidazolyl, indolyl, isoquinolyl and quinolyl.

Also, in the context of this invention, a chemical compound comprising a tertiary amino group may also be made quaternary (quaternized) using an alkylation agent, in particular an alkyl halide, preferably the chloride, bromide or iodide of methyl or ethyl.

Specific Examples

In its most preferred embodiment, the chemical compound of the invention is one selected from those described in the working examples or in Tables 1–8, below.

TABLE 1

Chemical Compounds of Formula I

| Compound | A | Example |
|---|---|---|
| 1a* | 1,3-diethylcyclohexyl | 2 |
| 1b | —(CH$_2$)$_6$— | 1 |
| 1c | —(CH$_2$)$_4$— | 1 |
| 1d | —(CH$_2$)$_3$— | 1 |
| 1e | —(CH$_2$)$_2$— | 2 |
| 1f | 1,4-diethylphenyl | 2 |
| 1g | 1,3-diethylphenyl | 2 |
| 1h | 1,3-dimethylphenyl | 2 |
| 1i | dimethylbiphenyl | 2 |
| 1j | 1,5-cyclooctyl | 18 |

*cis/trans mixture

TABLE 2

Chemical Compounds of Formula II

| Compound | R$_1$ | R$_2$ | Example |
|---|---|---|---|
| 2a | 4-(4-chlorophenyl)-2-methylthiazol-yl | H | 17/A |
| 2b | 4-(dimethylamino)phenylethyl | CF$_3$ | 17/A |
| 2c | 2-methyl-4-phenylthiazol-yl | H | 17/A |
| 2d | 1,3,5-trimethyl-4-(m-tolyl)pyrazol-yl | H | 17 |
| 2e | 4-(thiazol-2-ylamino)phenyl | H | 17/A |
| 2f | 4-(N'-phenylguanidino)phenyl | H | 17/A |

TABLE 3
Chemical Compounds of Formula III
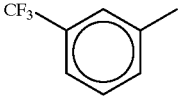
| Compound | R₁ | R₂ | Example |
|---|---|---|---|
| 3a | 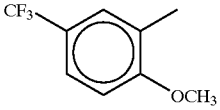 | 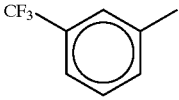 | 17/E |
| 3b |  | 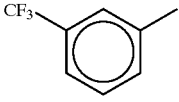 | 17/F |
| 3c | 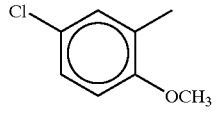 | 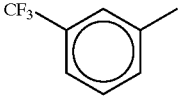 | 17/E |
| 3d | 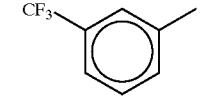 | 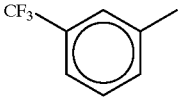 | 17/E |
| 3e | 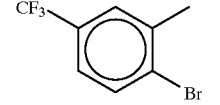 | 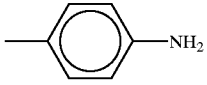 | 17/F |
| 3f | 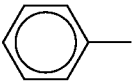 | H | 6 |
| 3g | 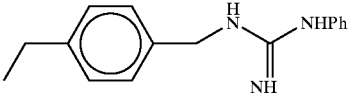 | 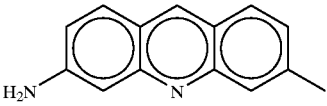 | 7 |
| 3h |  | H | 8 |

TABLE 4
Chemical Compounds of Formula IV
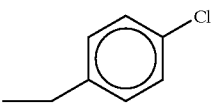
| Compound | R₁ | R₂ | R₃ | Example |
|---|---|---|---|---|
| 4a | 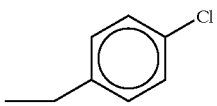 | 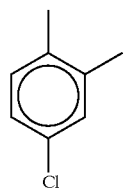 | 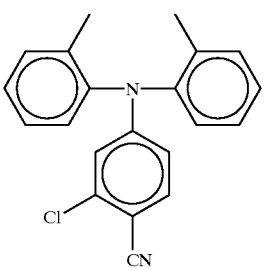 | 17/F |
| 4b | H | H | 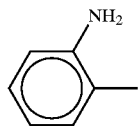 | 17/G |
| 4c | 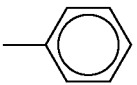 | 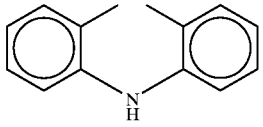 | —CH₂CH₂— | 17/G |
| 4d | H | H | 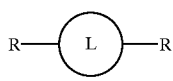 | 17/G |
TABLE 5
Chemical Compounds of Formula V
| Compound | L | R | Example |
|---|---|---|---|
| 5a | 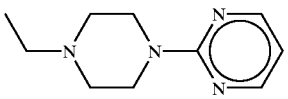 |  | 13 |
| 5b | 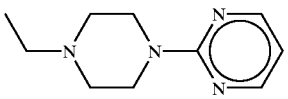 | 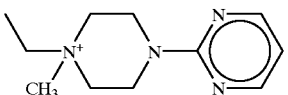 | 14 |

TABLE 5-continued

Chemical Compounds of Formula V

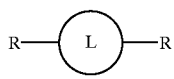

| Compound | L | R | Example |
|---|---|---|---|
| 5c | piperazine (N-methyl on both N) | 2-methyl-1-benzyl-benzimidazole | 15 |

TABLE 6

Chemical Compounds of Formula VI

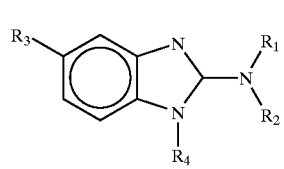

| Compound | R₁ | R₂ | R₃ | R₄ | Example |
|---|---|---|---|---|---|
| 6d | CH₃ | CH₃ | CF₃ | 4-chlorobenzyl | 16 |

TABLE 7

Chemical Compounds of Formula VII

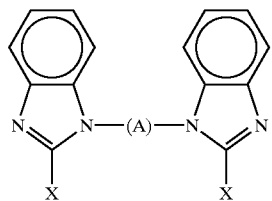

| Compound | X | A | Example |
|---|---|---|---|
| 7a | Cl | 1,4-cyclohexyl-bis(methylene) | 11 |

TABLE 7-continued

Chemical Compounds of Formula VII

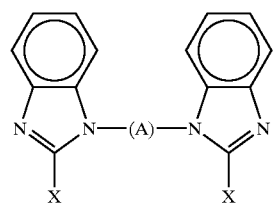

| Compound | X | A | Example |
|---|---|---|---|
| 7b | pyrrolidinyl | 1,4-cyclohexyl-bis(methylene) | 12 |
| 7c | morpholinyl | 1,4-cyclohexyl-bis(methylene) | 13 |
| 7d | N-methylpiperazinyl | 1,4-cyclohexyl-bis(methylene) | 14 |
| 7e | H | 1,3-phenylene-bis(methylene) | 9 |

TABLE 8

Chemical Compounds of Formula VIII (VIII)

| Compound | X | A | B | Example |
|---|---|---|---|---|
| 7f | H | (meta-xylylene) | (para-xylylene) | 10 |

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known is methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization, of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The chemical compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallization, distillation, chromatography, etc.

Biological Activity

The chemical compounds of the invention have been subjected to in vitro experiments and found particularly useful as potassium channel blocking agents. More particularly the compound of the invention are capable of selectively blockade of SK channels, e.g. SK1, SK2 and/or SK3 channels.

As described in the working examples, the compounds tested all showed a biological activity determined as $IC_{50}$ in the sub-micromolar and low micromolar range, i.e. of from below 1 to above 10 $\mu$M. Preferred compounds of the invention show a biological activity determined as described herein in the in the sub-micromolar and micromolar range, i.e. of from below 1 to about 100 $\mu$M.

Therefore, in another aspect, the invention relates to the use of a chemical compound of the invention for the manufacture of medicaments, which medicament may be useful for the treatment or alleviation of a disease or a disorder associated with the activity of potassium channels, in particular SK channels.

In a more preferred embodiment, the chemical compound of the invention may be use for the manufacture of medicaments for the treatment or alleviation of diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

Pharmaceutical Compositions

In yet another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the chemical compound of the invention, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, nasal, topical (including buccal and sub-lingual), transdermal, vaginal or parenteral (including intramuscular, sub-cutaneous and intravenous) administration, or those in a form suitable for administration by inhalation or insufflation.

The chemical compound of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The active ingredient may be administered in one or several doses per day. It is presently contemplated that compositions containing of from about 0.1 to about 500 mg of active ingredient per unit dosage, preferably of from about 1 to about 100 mg, most preferred of from about 1 to about 10 mg, are suitable for therapeutic treatments.

Methods of Treatment

In another aspect the invention relates to a method of treating or alleviating a disorder or disease of a living animal body, including a human, which disorder or disease is responsive to blockade of the potassium channel, in particular the SK channel, which method comprises comprising administering to such a living animal body, including a human, in need thereof a therapeutically-effective amount of a compound of the invention.

The in a preferred embodiment of the method of the invention, the disease or disorder is asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples which are not intended to be in any way limiting to the scope of the invention as claimed.

Example 1

General Reaction Scheme for the Syntheses of Compounds 1a–1f (see Table 1)

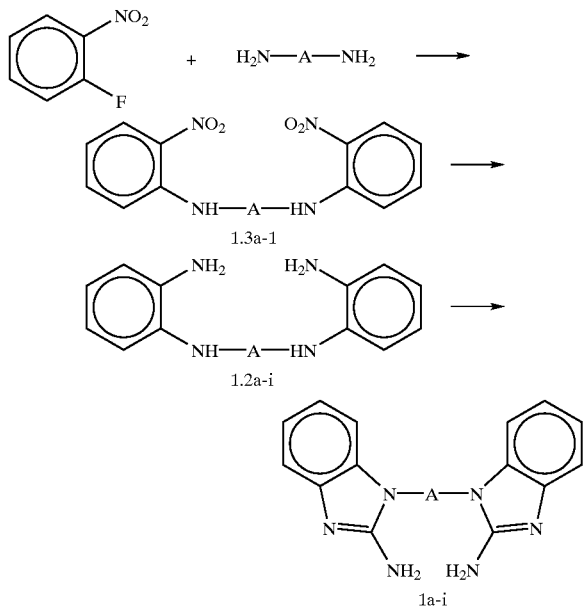

1,4-Bis(2-aminobenzimidazol-1-yl)butane, 2HCl (Compound 1c). A suspension of 1.2c·2HCl (1.1 g, 3.2 mmol) in anhydrous DMF (10 ml) was wrapped in alu-foil to exclude light. A solution of cyanogen bromide (0.7 g, 6.6 mmol) in anhydrous DMF (5 ml) was added dropwise. The mixture was stirred in a nitrogen atmosphere at ambient temperature for three days, whereafter it was poured into ice-water. The precipitate was filtered off, washed with water and dried to leave 1c (0.42 g). M.p. 292–294° C.

1,6-Bis(2-aminobenzimidazol-1-yl)hexane, 2HCl (Compound 1b) was prepared analogously from 1.2b. M.p. 145–147° C.

1,3-Bis(2-aminobenzimidazol-1-yl)propane (Compound 1d) was prepared analogously from 1.2d. The product was isolated as the free base. M.p. 220° C. (with decomposition).

Example 2

1,3-Bis[(2-aminobenzimidazol-1-yl)methyl]cyclohexane (Compound 1a) was prepared from 1.2a as described in Example 1 with the following modifications: The solvent was anhydrous NMP. The reaction time was 24 hours. At the end of the reaction the mixture was poured into water and rendered alkaline by addition of aqueous sodium carbonate. The precipitate was filtered off and purified by column chromatography on silica gel using a mixture of dichloromethane, methanol and aqueous ammonia (9:1:0.1 v/v/v) as the eluent. Yield: 0.28 g (cis/trans mixture) which gradually decomposed upon melting.

α,α'-Bis(2-aminobenzimidazol-1-yl)-para-xylene (Compound 1f) was prepared analogously from 1.2f. M.p. 287–289° C.

α,α'-Bis(2-aminobenzimidazol-1-yl)-meta-xylene (Compound 1g) was prepared analogously from 1.2g. M.p. 279–280° C.

3,3'-Bis(2-aminobenzimidazol-1-yl)biphenyl (Compound 1i) was prepared analogously from 1.2i. M.p. 160–163° C.

1,3-Bis(2-aminobenzimidazol-1-yl)benzene (Compound 1h) was prepared analogously from 1.2h using DMF as the solvent. M.p. 270–275° C.

1,2-Bis(2-aminobenzimidazol-1-yl)ethane (Compound 1e) was prepared from 1.2e in analogy with Example 2 using DMF as the solvent and a total of four equivalent of cyanogen bromide. The reaction time was 6 days. Yield: 0.13 g. M.p. 257–258° C.

Example 3

N,N'-Bis(2-aminophenyl)-1,4-butanediamine, 2HCl (Compound 1.2c): To a suspension of 1.3c (1.2 g, 3.64 mmol) in a mixture of abs. EtOH and dichloromethane (50 ml, 9:1) was added Pd-catalyst (0.1 g, 5% Pd on activated carbon). The mixture was hydrogenated at ambient pressure until the $H_2$-uptake had ceased and thereafter filtered through celite. The filtrate was concentrated to a small volume under reduced pressure. Ethereal hydrogen chloride, was added, and the product was isolated by filtration. Yield: 1.14 g.

1,3-Bis(N-(2-aminophenyl)methylamine)cyclohexane, 2HCl (Compound 1.2a) was prepared analogously from 1.3a.

N,N'-Bis(2-aminophenyl)-1,6-hexanediamine, 2HCl (Compound 1.2b) was prepared analogously from 1.3b.

N,N'-Bis(2-aminophenyl)-1,3-propanediamine, 2HCl (Compound 1.2d) was prepared analogously from 1.3d.

N,N'-Bis(2-aminophenyl)ethylendiamine, 2HCl (Compound 1.2e) was prepared analogously from 1.3e.

N,N'-Bis(2-aminophenyl)-meta-xylylenediamine, 2HCl (Compound 1.2g) was prepared analogously from 1.3g.

N,N'-Bis(2-aminophenyl)-1,3-phenylenediamine, 2HCl (Compound 1.2h) was prepared analogously from 1.3h.

N,N'-Bis(2-aminophenyl)-3,3'-diaminobiphenyl, 2HCl (Compound 1.2i) was prepared analogously from 1.3i.

Example 4

N,N'-Bis(2-aminophenyl)-para-xylylenediamine (Compound 1.2f): To a suspension of 1.3f (8.7 g, 23.0 mmol) in a mixture of abs. EtOH and THF (500 ml, 1:1) was added sodium sulphide nonahydrate (55.3 g, 0.23 mol) and ammonium chloride (12.3 g, 0.23 mol). The resulting mixture was heated to reflux for three days. The solvent was removed by evaporation and the residue was triturated with water. The crude product was filtered off and extracted with a refluxing mixture of diethyl ether and methanol (200 ml, 1:1). The cooled extract was concentrated and purified by column-chromatography on silica gel using a mixture of ethyl acetate and petroleum ether (1:1 v/v) as the eluent. Yield: 1.87 g.

Example 5

N,N'-Bis(2-nitrophenyl)-1,4-butanediamine (Compound 1.3c): A mixture of 1,4-butanediamine (0.51 ml, 5.0 mmol), 1-fluoro-2-nitrobenzene (1.1 ml, 10.0 mmol) and triethylamine (1.39 ml, 10.0 mmol) in anhydrous DMF (5 ml) was heated to 100° C. over-night. The cooled mixture was poured into ice-water. The product was filtered off, washed with water and dried to yield 1.22 g (24%).

1,3-Bis[N-(2-nitrophenyl)aminomethyl]cyclohexane (Compound 1.3a) was prepared analogously from 1,3-bis(aminomethyl)cyclohexane.

N,N'-Bis(2-nitrophenyl)-1,6-hexanediamine (Compound 1.3b) was prepared analogously from 1,6-hexanediamine.

N,N'-Bis(2-nitrophenyl)-1,3-propanediamine (Compound 1.3d) was prepared analogously from 1,3-propanediamine.

N,N'-Bis(2-nitrophenyl)ethylenediamine (Compound 1.3e) was prepared analogously from ethylenediamine.

N,N'-Bis(2-nitrophenyl)-para-xylylenediamine (Compound 1.3f) was prepared analogously from para-xylylenediamine.

N,N'-Bis(2-nitrophenyl)-meta-xylylenediamine (Compound 1.3g) was prepared analogously from meta-xylylenediamine.

N,N'-Bis(2-nitrophenyl)-1,3-phenylenediamine (Compound 1.3h) was prepared analogously from 1,3-phenylenediamine.

N,N'-Bis(2-nitrophenyl)-3,3'-diaminobiphenyl (Compound 1.3i) was prepared analogously from 3,3'-diaminobiphenyl.

Example 6

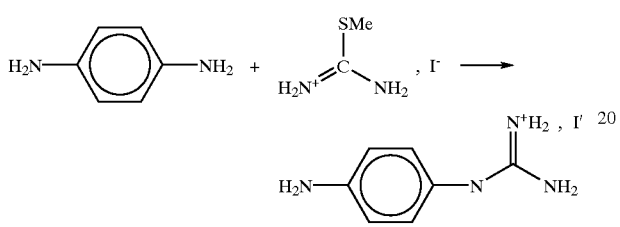

1-(4-Aminophenyl)guanidine, HI (Compound 3f): To a solution of 1,4-phenylenediamine (1.08 g, 10.0 mmol) in a mixture of abs. EtOH (20 ml) and THF (10 ml) was added methyl thiuronium iodide (1.69 g, 7.75 mmol). The mixture was heated to 60° C. for 3 days. After cooling the solvent was removed by evaporation and the residue was extracted with water. The extract was evaporated to dryness and the residue was washed with ether to leave 3f (1.93 g). M.p. 195–197° C.

Example 7

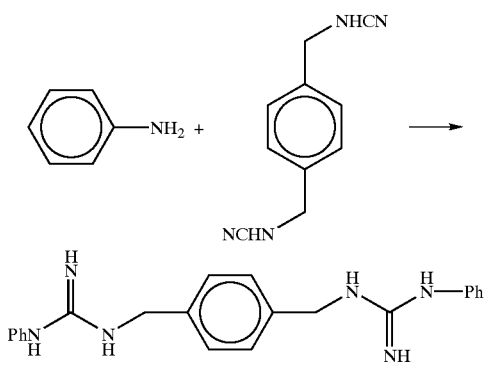

α,α'-Bis(3-phenylguanidine-1-yl)-para-xylene, 2HCl (Compound 3g): To a solution of aniline (1.37 ml, 15.0 mmol) in DMF (25 ml) was added concentrated hydrochloric acid (0.23 ml). The mixture was stirred for 30 min prior to addition of a suspension of N,N'-dicyano-para-xylylenediamine (0.7 g, 3.76 mmol) in DMF (10 ml). The resulting mixture was heated to 100° C. for four days. The solvent was removed by evaporation under reduced pressure and the residue was extracted with EtOH. The concentrated extract was column-chromatographied on silica gel using a mixture of ethylacetate and petroleum ether (1:1) as the eluent, Etheral hydrogen chloride was added to the product-containing eluate. The product was filtered off and dried. Yield: 0.18 g. M.p. 204–207° C.

N,N'-dicyano-para-xylylenediamine: To a suspension of para-xylylenediamine (1.88 g, 3.8 mmol) in THF (50 ml) was added a solution of cyanogenbromide (1.06 g, 10.0 mmol in THF (50 ml). The reaction vessel was wrapped in alu-foil and the mixture was left with stirring at ambient temperature for three days. The mixture was filtered and the filtrate was evaporated to dryness to leave the desired product (0.71 g).

Example 8

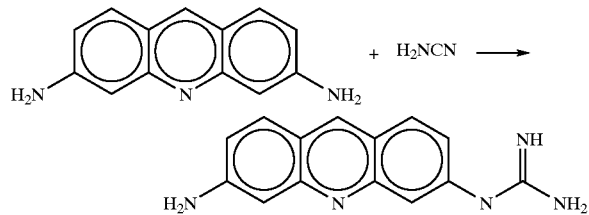

6-Amino-3-guanidinoacridine, HCl (Compound 3h): To a solution of 3,6-diaminoacridine (0.5 g, 1.0 mmol) in concentrated hydrochloric acid (10 ml) was added cyanamide (0.18 g, 4.3 mmol). The mixture was heated to 100° C. for 6 days. The cooled mixture was poured into ice-water and rendered alkaline by addition of aqueous sodium hydroxide. The precipitate was filtered off and fractionated by column-chromatography on silica gel using a mixture of acetonitril, acetic acid and water (4:1:1 v/v/v) as the eluent. The product-containing fractions were concentrated and the product precipitated upon addition of etheral hydrogen chloride. Yield: 30 mg. M.p. above 305° C.

Example 9

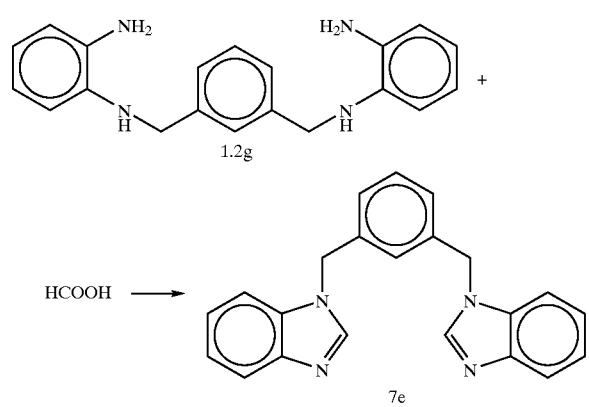

α,α'-Bis(1-benzimidazolyl)-meta-xylene (Compound 7e): A solution of 1.2 g (1.39 g, 4.37 mmol) in formic acid (5 ml) was heated to 80° C. for 30 min. Excess formic acid was removed by evaporation and the residue was stirred with ice-cold aqueous sodium carbonate. The product was filtered off, washed with water and dried. Yield: 1.20 g.

Example 10

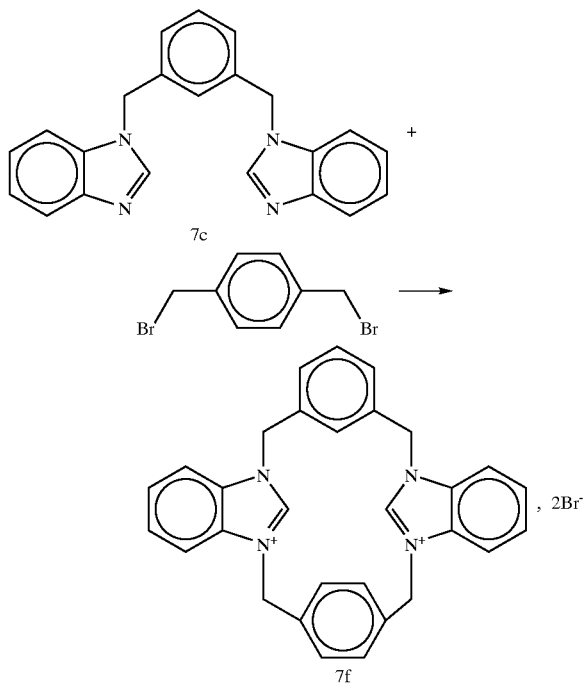

1,1'-(α,α'-para-xylylene)-3,3'-(α,α'-meta-xylylene)-bis(benzimidazolium) Bromide (Compound 7f): A mixture of 7e (0.46 g, 1.38 mmol) and α,α'-dibromo-para-xylene (0.36 g, 1.38 mmol) in DMF (70 ml) was heated to 100° C. overnight. The solvent was removed under reduced pressure and the crystalline residue was washed with dichloromethane to leave 7f (0.76 g). M.p. 292–294° C.

Example 11

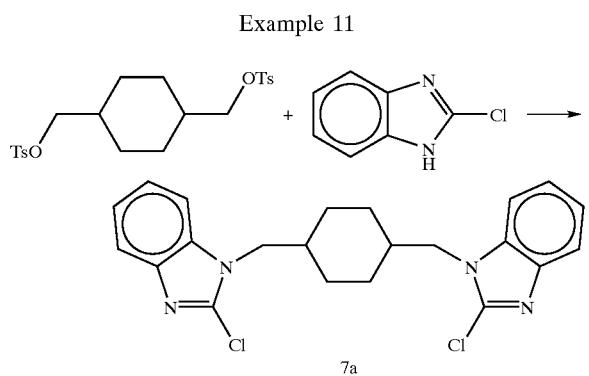

cis,trans-1,4-Bis[(2-chlorobenzimidazol-1-yl)methyl]cyclohexane (Compound 7a): A mixture of 1,4-bis(p-toluenesulfonyloxymethyl)cyclohexane (1.10 g, 2.43 mmol), 2-chlorobenzimidazole (0.74 g, 4.85 mmol) and potassium carbonate (0.67 g, 4.85 mmol) in abs. EtOH (20 ml) was heated to 75° C. for two days. The cooled mixture was poured into water and the precipitate was filtered off, washed with water and dried to yield 7a (0.61 g). M.p. 247–253° C.

Example 12

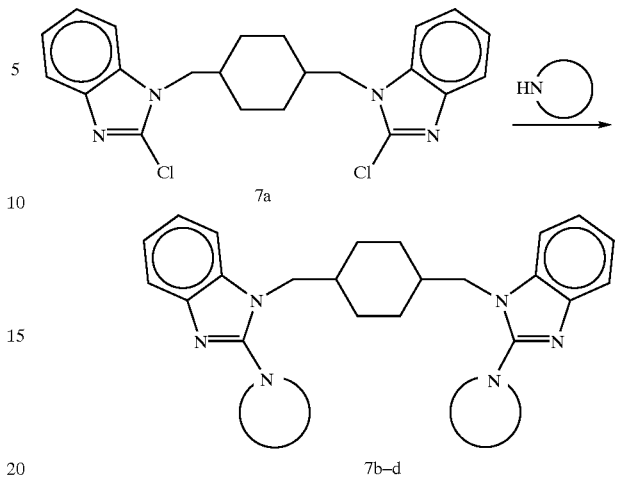

cis,trans-1,4-Bis[2-(1-pyrrolidinyl)benzimidazol-1-yl)methyl]cyclohexane (Compound 7b): A mixture of 7a (0.25 g, 0.61 mmol) and pyrrolidine (2 ml, 24 mmol) was heated to 80° C. for 2 hours. After cooling the mixture was poured into water and the precipitate was filtered off. This crude product was recrystallized from a mixture of 2-propanol and dichloromethane (9:1 v/v) to yield 7b (0.12 g). M.p. 258–260° C.

cis,trans-1,4-Bis[(2-(4-morfolinyl)benzimidazol-1-yl)methyl]cyclohexane, 2HCl (Compound 7c) was prepared analogously from 7a and morpholine. Isolated as the hydrochloride. M.p. 286–288° C.

cis,trans-1,4-Bis[(2-(1-methylpiperazine-4-yl)benzimidazol-1-yl)methyl]cyclohexane (Compound 7d) can be prepared analogously from 7a and 1-methylpiperazine.

Example 13

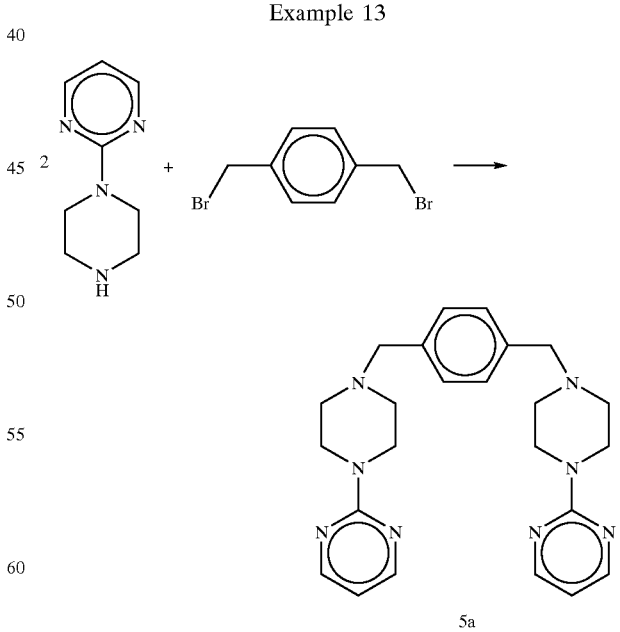

α,α'-Bis(1-(2-pyrimidyl)piperazin-4-yl)-para-xylene (Compound 5a): A mixture of 1(2-pyrimidyl)piperazine, 2HCl (2.0 g, 8.43 mmol), α,α'-dibromo-para-xylene (1.11 g, 4.21 mmol) and triethylamine (2.34 ml) in DMF (25 ml) was heated to 100° C. overnight. The cooled mixture was filtered and the precipitate was dissolved in water and rendered alkaline by addition of aqueous sodium hydroxide. The product was filtered off, washed with water and dried. Yield: 1.91 g. M.p. 193–195° C.

Example 14

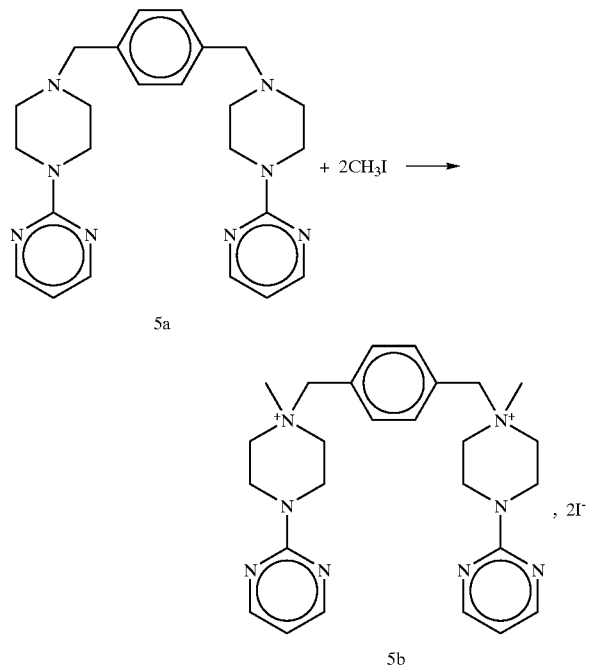

α,α'-Bis(1-(2-pyrimidyl)-4-methylpiperazinium-4-yl)-para-xylene Iodide (Compound 5b). To a suspension of 5a (0.75 g, 1.74 mmol) in a mixture of dichloromethane (10 ml) and DMF (1 ml) was added iodimethane (0.22 ml, 3.53 mmol) and the mixture was stirred at ambient temperature for three days. The product was filtered off, washed with dichloromethane and dried. Yield: 0.63 g. M.p. above 310° C.

Example 15

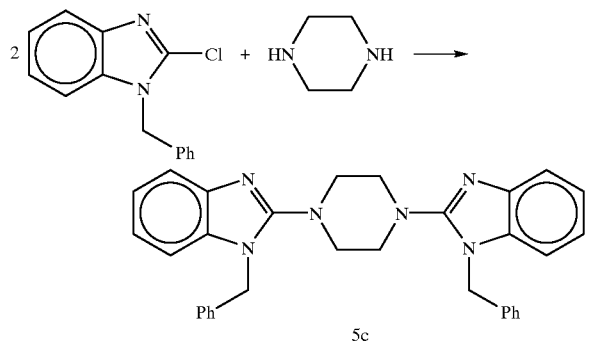

1,4-Bis(1-benzylbenzimidazol-2-yl)piperazine (Compound 5c): A mixture of 1-benzyl-2-chlorobenzimidazole (1.21 g, 5.0 mmol), piperazine (0.22 g, 2.5 mmol) and potassium carbonate (0.69 g, 5.0 mmol) in DMF (10 ml) was heated to reflux for three days. The cooled mixture was poured into ice-water. The precipitate was filtered off and washed with refluxing ethyl acetate to leave 5c. Yield: 0.46 g. M.p. 247–248° C.

Example 16

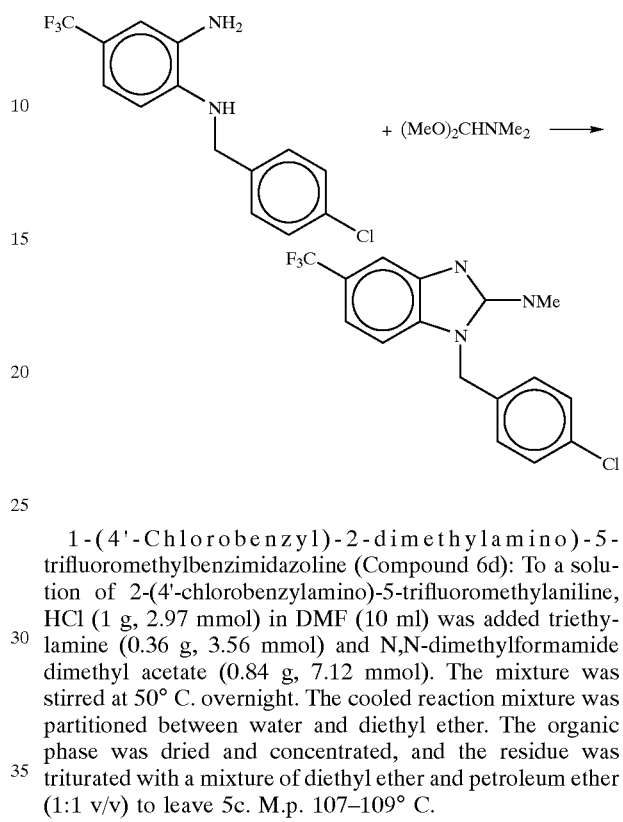

1-(4'-Chlorobenzyl)-2-dimethylamino)-5-trifluoromethylbenzimidazoline (Compound 6d): To a solution of 2-(4'-chlorobenzylamino)-5-trifluoromethylaniline, HCl (1 g, 2.97 mmol) in DMF (10 ml) was added triethylamine (0.36 g, 3.56 mmol) and N,N-dimethylformamide dimethyl acetate (0.84 g, 7.12 mmol). The mixture was stirred at 50° C. overnight. The cooled reaction mixture was partitioned between water and diethyl ether. The organic phase was dried and concentrated, and the residue was triturated with a mixture of diethyl ether and petroleum ether (1:1 v/v) to leave 5c. M.p. 107–109° C.

Example 17

All reactions in this example involving air sensitive reagents or intermediates were performed under nitrogen and in anhydrous solvents. Magnesium sulphate was used as drying agent in the workup-procedures and solvents were evaporated under reduced pressure.

2-Amino-1-[3-(1,3,5-trimethylpyrazol-4-yl)phenyl] benzimidazole (Compound 2d).

A mixture of 2-(3-(2-amino-1-benzimidazolyl)phenyl)-1,3,2-dioxaborinane (2.0 g, 6.82 mmol), 4-bromo-1,3,5-trimethylpyrazole (1.29 g, 6.82 mmol), tetrakis (triphenylphosphine)-palladium(0) (0.24 g, 0.20 mmol), sodium hydrogen carbonate (2.29 g, 27.3 mmol), water (27 ml) and 1,2-dimethoxyethane (54 ml) was stirred at reflux overnight. Aqueous sodium hydroxide (50 ml) was added and the mixture was extracted twice with ethyl acetate (50 ml). The crude extract was purified by chromatography using silica gel and a mixture of ethanol (4%) and dichloromethane as eluent. The product was isolated as the free base. Yield 0.60 g, 28%. M.p. 198–200° C.

Method A

2-Amino-1-(4-dimethylaminobenzyl)-5-trifluoromethylbenzimidazole (Compound 2b).

A mixture of 2-amino-N-(4-dimethylaminobenzyl)-4-trifluoromethylaniline (5.2 g, 16.8 mmol), cyanogen bromide (2.31 g, 21.8 mmol) in DMF (75 ml) was stirred for three days at room temperature. Water (100 ml) was added, and the mixture was filtered. The filtrate was made alkaline with sodium hydroxide (2 M, 100 ml). The mixture was extracted twice with ethyl acetate (100 ml). The crude extract was purified by chromatography using silica gel and a mixture of ethanol (4%) and dichloromethane as eluent. The product was isolated as the free base. Yield 0.92 g, 16%. M.p. 184–186° C.

2-Amino-1-[4-(4-chlorophenyl)-2-thiazolyl] benzimidazole Hydrochloride (Compound 2a) was prepared from 2-amino-N-[4-(4-chlorophenyl)-2-thiazolyl]-aniline according to method A. M.p. 220–223° C.

2-Amino-1-(4-phenyl-2-thiazolyl)benzimidazole (Compound 2c) was prepared from 2-amino-N-(4-phenyl-2-thiazolyl)aniline according to method A. M.p. 229–231° C.

2-Amino-1-(4-(N-(2-thiazolyl)amino)phenyl) benzimidazole (Compound 2e) was prepared from 2-amino-4-(N-(2-thiazolyl)amino)phenyl)aniline according to method A. M.p. 218–220° C.

2-Amino-1-(4-acetamidophenyl)benzimidazole was prepared from 2-amino-N-(4-acetamidophenyl)aniline according to method A. M.p. 246–248° C.

2-(3-(2-Amino-1-benzimidazolyl)phenyl)-1,3,2-dioxaborinane was prepared according to method A from 2-amino-3'-(1,3,2-dioxaborinan-2-yl)diphenylamine. M.p. 150–155° C.

2-Amino-1-(4-aminophenyl)benzimidazole Hydrochloride.

2-Amino-1-(4-acetamidophenyl)benzimidazole (1.78 g, 6.68 mmol) was refluxed in hydrochloric acid (25 ml) overnight. The crude mixture was evaporated and triturated with diethyl ether. Yield 1.68 g, 96%, M.p. 258–260° C.

1-(4-(2-Aminobenzimidazol-1-yl)phenyl)-3-phenylguanidine Hydrochloride (Compound 2f).

A mixture of 2-Amino-1-(4-aminophenyl)benzimidazole Hydrochloride (1.58 g, 6.06 mmol), phenylcyanamide (2.79 g, 23.6 mmol) and acetonitrile (10 ml) was refluxed for 3 days. The solid product was filtered off. The product was recrystallized from acetonitrile (300 ml). Yield 1.3 g, 57%. M.p. 265–267° C.

Method B

2-Amino-N-(4-dimethylaminobenzyl)-4-trifluoromethylaniline.

A mixture of N-(4-dimethylaminobenzyl)-2-nitro-4-trifluoromethylaniline (6.0 g, 17.7 mmol), palladium on carbon (0.70 g, 5%), ethanol (200 ml) and tetrahydrofurane (175 ml) was stirred under hydrogen until 1.19 l was consumed. The reaction mixture was filtered through a celite pad and evaporated. Yield 5.35 g, 98%. M.p. 160–162° C.

2-Amino-N-[4-(4-chlorophenyl)-2-thiazolyl]aniline was prepared from N-[4-(4-chlorophenyl)-2-thiazolyl]-2-nitroaniline.

2-Amino-N-(4-phenyl-2-thiazolyl)aniline hydrochloride was prepared from 2-nitro-N-(4-phenyl-2-thiazolyl)aniline according to method B. M.p. 189–190° C.

2-Amino-N-(4-acetamidophenyl)aniline was prepared from N-(4-acetamidophenyl)-2-nitroaniline according to method B. Isolated as an oil.

2-Amino-3'-(1,3,2-dioxaborinan-2-yl)diphenylamine was prepared from 3'-(1,3,2-dioxaborinan-2-yl)-2-nitrodiphenylamine according to method C. M.p. 220–222° C. (for the hydrochloride).

Method C

2-Amino-N-(4-(2-thiazolyiamino)phenyl)aniline.

A mixture of 2-nitro-N-(4-(2-thiazolylamino)phenyl) aniline (1.2 g, 3.8 mmol), sodium sulfide nona hydrate (4.61, 19.2 mmol), ammonium chloride (1.03 g, 19.2 mmol) and ethanol (40 ml) was stirred at reflux for 40 h. Water (50 ml) was added, the mixture was stirred and filtered. Yield 0.49 g, 46%. M.p. 184–186° C.

N-(4-Dimethylaminobenzyl)-2-nitro-4-trifluoromethylaniline.

A mixture of 4-chloro-3-nitrobenzotrifluoride (5.05 g, 22.4 mmol), 4-(dimethylamino)-benzylamine dihydrochloride (5.0 g, 22.4 mmol), potassium carbonate (9.29 g, 76.2 mmol) and dimethylformamide (60 ml) was stirred at room temperature for 3 days. Water (60 ml) was added and the mixture was stirred for 0.5 h followed by filtration. The crystalline product was triturated with petroleum ether. Yield 6.08 g, 80%. M.p. 158–160° C.

Method D

2-Nitro-N-(4-phenylthiazol-2-yl)aniline.

A mixture of 2-amino-4-phenylthiazole (12.5 g, 80.9 mmol), 1-fluoro-2-nitrobenzene (12.5 g, 89.0 mmol), potassium carbonate (13.4 g, 97.1 mmol) was stirred at 150° C. for 24 h. Water (100 ml) was added and the mixture was extracted twice with 1,2-dichloroethane (50 ml). The crude extract was purified by chromatography on silica gel using toluene as eluent. The product was isolated as the free base. Yield 7.95 g, 33%. M.p. 114–116° C.

N-[4-(4-Chlorophenyl)-2-thiazolyl]-2-nitroaniline was prepared according to method D.

2-Nitro-N-(4-aminophenyl)aniline was prepared according to method D. M.p. 110–112° C.

2-Nitro-N-(4-acetamidophenyl)aniline was prepared according to method D. M.p. 164–166° C.

3-(2-Nitrophenylamino)phenylboronic Acid was prepared according to method D using dimethylformamide as solvent and 90° C. as reaction temperature. M.p. 195–196° C.

2-Nitro-N-(4-(2-thiazolylamino)phenyl)aniline.

2-Nitro-N-(4-aminophenyl)aniline (5.0 g, 21.8 mmol), 2-bromothiazole (3.58 g, 21.8 mmol) and potassium carbonate (3.01 g, 21.8 mmol) was stirred at 150° C. for 24 h. Water (250 ml) was added and the mixture was extracted with ethyl acetate (250 ml). The crude extract was purified by chromatography using silica gel and a mixture of ethanol (4%) and dichloromethane as eluent. The product was isolated as the free base. Yield 1.47 g, 22%. M.p. 195–197° C.

3'-(1,3,2-Dioxaborinan-2-yl)-2-nitrodiphenylamine.

A mixture of 2-nitrodiphenylamine-3'-boronic acid (27.0 g, 105 mmol), 1,3 propanediol (9.55 g, 126 mmol), and toluene (500 ml) was refluxed for 2 h with a Dean-Stark water separator attached. The solvent was evaporated and the product was obtained as a yellow oil. Yield 31 g, 99%.

Method E 1-(2-Methoxy-5-(trifluoromethyl)phenyl)-3-(3-(trifluoromethyl)phenyl)guanidine Compound 3a).

A mixture of 3-cyanamidobenzotrifluoride (0.40 g, 2.15 mmol), 2-methoxy-5-triflouromethylaniline hydrochloric acid salt (0.53 g, 2.33 mmol) and acetonitrile (20 ml) was stirred at reflux for 40 h. The solvent was evaporated. Dichloromethane (50 ml) was added and the mixture was washed with saturated aqueous sodium hydrogen carbonate (50 ml). The organic phase was purified by chromatography using silica gel and a mixture of methanol (10%) and dichloromethane as eluent. The product was isolated as the free base. Yield 0.40 g, 49%. M.p. 45–47° C.

1-(5-Chloro-2-methoxyphenyl)-3-(3-(trifluoromethyl) phenyl)guanidine (Compound 3c) was prepared according to method E. M.p. 94–96° C.

1,3-Bis(3-(trifluoromethyl)phenyl)guanidine (Compound 3d) was prepared according to method E. M.p. 108–110° C.

3-Cyanamidobenzotrifluoride.

A mixture of 3-aminobenzotrifluoride (15.0 g, 93.1 mmol), cyanogen bromide (12.2 g, 129 mmol) and diethyl ether was stirred at reflux for 40 h. The crude mixture was purified by chromatography using silica gel and a mixture of petroleum ether and dichloromethane as eluent (1:1). The product was isolated as the free base. Yield 5.2 g, 25%.

Method F 1-(4-Chlorobenzyl)-3-(3-triflouromethylphenyl) guanidine (Compound 3b).

A mixture of 3-cyanamidobenzotrifluoride (1.20 g, 6.45 mmol) and 4-chlorobenzylamine hydrochloride (1.26 g, 7.09 mmol) was stirred at 150° C. for 40 h. Dichloromethane (100 ml) was added and the mixture was washed with saturated aqueous sodium hydrogen carbonate (100 ml). The organic phase was purified by chromatography using silica gel and a mixture of methanol (10%) and dichloromethane as eluent. The product was isolated as the free base. Yield 1.05 g, 50%. M.p. 103–105° C.

1-(2-Bromo-5-(trifluoromethyl)phenyl)-3-(5-(trifluoromethyl)phenyl)guanidine (Compound 3e) was prepared according to method F at 130° C. for 15 h. Isolated as an oil.

5-Chloro-1,3-bis(4-chlorobenzyl)-2-iminobenzimidazoline (Compound 4a).

A mixture of 2-amino-5-chloro-benzimidazole (9.4 g, 56.1 mmol), 4-chlorobenzylchloride (9.93 g, 61.7 mmol), potassium carbonate (15.5 g, 112 mmol) and dimethyl formamide (150 ml) was stirred at 50° C. for 20 h. Water (150 ml) was added and the product was filtered off. The crude product was purified by chromatography using silica gel and a mixture of ethanol (5%) and dichloromethane as eluent. The product was isolated as the free base. Yield 0.37 g, 2%. M.p. 175–177° C.

2-Amino-5-chlorobenzimidazole.

To a mixture of 2-amino-4-chloroaniline (15.2 g, 106.6 mmol) and dimethylformamide (150 ml) was added cyanogen bromide (14.7 g, 138.6 mmol). The mixture was stirred for 3 days. Water (300 ml) was added, and some impurities were removed by filtration. Sodium hydroxide (212 ml, 2 M) was added to the filtrate and the mixture was extracted five times with ethyl acetate (50 ml). The organic phase was washed with sodium hydroxide (100 ml, 4M), dried and evaporated to dryness. The residue was finally triturated with petroleum ether to leave the product. Yield 9.4 g, 53%.

2-Amino-4-chloroaniline was prepared from 4-chloro-2-nitroaniline according to method B.

Method G

2-Chloro-5-(6-imino-5,6,7,12-tetrahydrodibenzo[d,g][1,3,6]triazocin-12-yl)benzonitrile (Compound 4b).

A mixture of N,N-bis(2-aminophenyl)-3-chloro-4-cyanoaniline (2.6 g, 7.76 mmol), cyanogen bromide (2.46 g, 23.3 mmol) and dimethylformamide (30 ml) was stirred at room temperature for 5 days. Water (100 ml) was added, and the aqueous phase was washed with diethyl ether (100 ml). To the aqueous phase was added sodium hydroxide (1 M, 100 ml), and the mixture was extracted twice with ethyl acetate (100 ml). The crude extract was purified by chromatography using silica gel and a mixture of ethanol (10%) and dichloromethane as eluent. The product was isolated as the free base. Yield 0.50 g, 28%. M.p. 225–228° C.

5,6,7,12-Tetrahydrodibenzo[d,g][1,3,6]triazocin-6-imine (Compound 4d) was prepared by method G. M.p. decomp.

N,N-Bis(2-aminophenyl)-3-chloro-4-cyanoaniline Hydrochloride

N,N-Bis(2-nitrophenyl)-3-chloro-4-cyanoaniline, palladium on carbon (0.70 g, 5%), ethanol (100 ml) was stirred under hydrogen until 2.5 l was consumed. The reaction mixture was filtered through a celite pad, hydrogen chloride in methanol (4M, 30 ml) was added and the solvent was removed by evaporation. The residue was triturated with ethyl acetate to leave the crystalline product. Yield 3.8 g, 53%. M.p. 184–187° C.

N,N-Bis(2-nitrophenyl)-3-chloro-4-cyanoaniline.

A mixture of 3-chloro-4-cyano-aniline (40.0 g, 262 mmol), 1-fluoro-2-nitrobenzene (40.7 g, 288 mmol) and potassium carbonate (36.2 g, 262 mmol) was stirred at 180° C. overnight with a water collector fitted to the condenser. Water (300 ml) was added followed by extraction with diethyl ether. The product was isolated by chromatography using dichloromethene as eluent. Yield 7.3 g, 7%. M.p. 165–167° C.

1-(2-Aminophenyl)-2-imino-3-phenyl-imidazolidine Hydrochloride (Compound 4c) was prepared from 2-imino-1-(2-nitrophenyl)-3-phenyl-imidazolidine according to method B. M.p. 228–230° C.

2-Imino-1-(2-nitrophenyl)-3-phenyl-imidazolidine was prepared from N-phenyl-N'-(2-nitrophenyl)ethylenediamine according to method A. M.p. 257–259° C.

N-phenyl-N'-(2-nitrophenyl)ethylenediamine.

A mixture of 1-fluoro-2-nitrobenzene(15.5 g, 110 mmol) and potassium carbonate (15.2 g, 110 mmol) was stirred and a mixture of N-methylpyrrolidone (20 ml) and N-phenylethylenediamine (15.0 g, 110 mmol) was added over 1 h at room temperature. The mixture was stirred for 1 h. Water (200 ml) was added crystals were filtered off and triturated with petroleum ether. Yield 14.7 g, 52%. M.p. 64–66° C.

Example 18

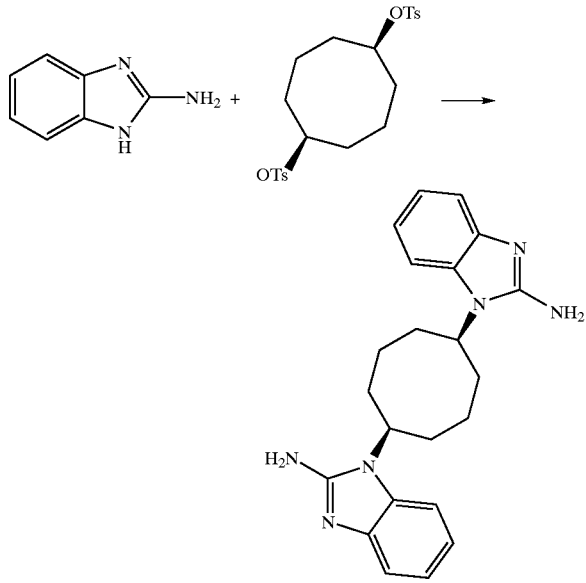

cis-1,5-bis(2-amino-1-benzimidazolyl)cyclooctane (Compound 1j).

To a hot (60° C.) solution of 2-aminobenzimidazole (0.22 g; 1.65 mmol) in DMF (25 ml) was added sodium hydride (70 mg; 60% dispersion in mineral oil), and the mixture was stirred for 30 minutes prior to addition of cis-1,5-bis(p-toluenesulfonyloxy)cyclooctane. The resulting mixture was stirred at 100° C. for four days, cooled and filtered. The filtrate was diluted with water and the precipitate was filtered off, washed with water and dried to yield the desired product (9 mg).

Example 19

Biological Activity

This example demonstrates the biological activity of the compounds of the invention. Compounds 1A and 1F of example 3, Compounds 1B of example 2, Compound 1J of example 19, and Compound 7F of example 11 were examined.

In this experiment, small-conductance $Ca^{2+}$-activated $K^+$ channels (SK channels, isoform 2) cloned from a rat cDNA library were stably expressed in HEK293 cells using standard procedures. The ionic current through the channels was recorded in the whole-cell mode of the patch-clamp technique.

Cells plated on coverslips are placed in a 15 $\mu$l perfusion chamber (flowrate~1 ml/min), mounted on a IMT-2 microscope equipped with Nomarski or Hoffmann optics. The microscopes are placed on vibration-free tables in grounded Faraday cages.

All experiments are performed at room temperature (20–22° C.). EPC-9 patch-clamp amplifiers (HEKA-electronics, Lambrect, Germany) are connected to Macintosh computers via ITC16 interfaces. Data are stored directly on the harddisk and analyzed by the IGOR software according to the manufacturer's instructions.

The whole-cell configuration of the patch clamp technique is applied. Shortly described, the tip of a borosilicate pipette (resistance 2–4 M$\Omega$) is gently (remote control system) placed on the cell membrane. Light suction results in a giga seal (pipette resistance increases to more than 1 G$\Omega$), and the cell membrane is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size), and the series resistance is in the range 3 to 6 M$\Omega$. Rs- as well as capacitance compensation are updated during the experiments (before each stimulus). All experiments with drifting Rs-values are discharged. Leak-subtractions are not performed.

Solutions

The extracellular (bath) solution contains (concentration in mM): 144 KCl, 2 $CaCl_2$, 1 $MgCl_2$, 10 HEPES (pH=7.4).

Test compounds are dissolved as 1000 times concentrated stock solutions in DMSO, and then diluted in the extracellular solution.

In the experiments where the effect of channel activators is quantified (test 475), the intracellular (pipette) solution has the following composition (concentration in mM):

144 KCl, 10 EGTA, 1.4 $MgCl_2$, 5.17 $CaCl_2$, and 10 HEPES (pH=7.2).

The calculated free concentration of $Ca^{2+}$ in this solution is 100 nM, and hat of $Mg^{2+}$ is 1 mM. In these experiments, the concentration of $CaCl_2$ is 7.6 mM and hat of $MgCl_2$ is 1.2 mM to give calculated free concentrations of 300 nM and 1 mM, respectively.

Quantification

After establishment of the whole-cell configuration, voltage-ramps (usually –100 to +100 mV) are applied to the cell every 5 sec. A stable baseline current is obtained within a period of 100–300 seconds and compounds are then added by changing to an extracellular solution containing the compound to be tested. Very little endogene current (<200 pA at 100 mV compared to 2–20 nA SK current) are activated under these circumstances in native HEK293 cells.

An $IC_{50}$ value is calculated from the kinetics of the block. The time-course of the decrease in current is fitted to the following equation:

$$I=I_0*(1-(C/C+(K_{off}/K_{on})))*(1-\exp(-(C*K_{on}+K_{off})*t)))$$

where $K_{off}$=off-rate in $s^{-1}$ $K_{on}$=on-rate in $M^{-1}s^{-1}$ $I_0$=basal current in nA C=drug concentration in $\mu$M $IC_{50}$ equals the ratio $K_{off}/K_{on}$.

The compounds of the invention tested in this experiment all showed a biological activity determined as IC50 in the sub-micromolar and low micromolar range, i.e. of from below 1 to above 10 $\mu$M.

What is claimed is:

1. A compound represented by formula VII,

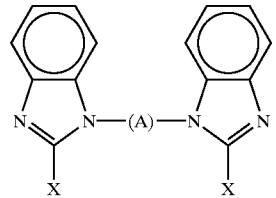

(VII)

or a pharmaceutically-acceptable addition salt thereof, wherein

X represents $NH_2$, and

A represents a radical of the formula —$(CH_2)_a$-D-$(CH_2)_b$—, wherein a and b, which may be identical or different, represent the number 0, 1, 2, 3, 4 or 5, and D represents a cycloalkyl group.

2. The compound of claim 1, wherein A represents (cis and/or trans)-1,5-cyclooctylene; or (cis and/or trans)-1,3-dimethylcyclohexane-α,α'-diyl.

3. The compound of claim 2, wherein said compound is 1,3-Bis((2-aminobenzimidazol-1-yl)methyl)cyclohexane; or cis-1,5-bis(2-amino-1-benzimidazolyl)cyclooctane; or a pharmaceutically-acceptable addition salt there of.

4. A pharmaceutical composition comprising an effective amount of a compound according to claim 1, or a pharmaceutically-acceptable addition salt thereof, together with at least one pharmaceutically-acceptable carrier or diluent.

5. The pharmaceutical composition according to claim 4, wherein the compound is 1,3-Bis((2-aminobenzimidazol-1-yl)methyl)cyclohexane; or cis-1,5-bis(2-amino-1-benzimidazolyl)cyclooctane.

* * * * *